US008972010B2

(12) United States Patent
Olson et al.

(10) Patent No.: US 8,972,010 B2
(45) Date of Patent: Mar. 3, 2015

(54) METHOD AND DEVICE FOR DETECTING NOISE (75) Inventors: Allan Olson, Spanga (SE); Lars Karlsson, Taby (SE); Marcus Berner, Stockholm (SE)

(73) Assignee: St. Jude Medical AB, Jarfalla (SE)

( * ) Notice: Subject to any disclaimer, the term of this patent is extended or adjusted under 35 U.S.C. 154(b) by 227 days.

(21) Appl. No.: 13/502,497

(22) PCT Filed: Nov. 30, 2009

(86) PCT No.: PCT/EP2009/066082
§ 371 (c)(1),
(2), (4) Date: Apr. 17, 2012

(87) PCT Pub. No.: WO2011/063858
PCT Pub. Date: Jun. 3, 2011

(65) Prior Publication Data
US 2012/0271373 A1 Oct. 25, 2012

(51) Int. Cl.
*A61N 1/00* (2006.01)
*A61N 1/37* (2006.01)
*A61N 1/365* (2006.01)

(52) U.S. Cl.
CPC .............. *A61N 1/37* (2013.01); *A61N 1/36521* (2013.01); *A61N 1/3718* (2013.01)
USPC ................................. 607/28; 607/27; 607/9

(58) Field of Classification Search
CPC ...... A61N 2001/083; A61N 1/37; A61N 1/08
USPC .................................................. 607/28, 27, 9
See application file for complete search history.

(56) References Cited

U.S. PATENT DOCUMENTS

| | | | |
|---|---|---|---|
| 5,871,509 A | 2/1999 | Noren | |
| 7,231,251 B2 | 6/2007 | Yonce et al. | |
| 2003/0009197 A1 | 1/2003 | Helland et al. | |
| 2004/0010294 A1 | 1/2004 | Kleine | |
| 2004/0049237 A1 | 3/2004 | Larson et al. | |
| 2006/0135886 A1 | 6/2006 | Lippert et al. | |

OTHER PUBLICATIONS

International Search Report—Int'l App. No. PCT/EP2009/066082; Int'l Filing Date: Nov. 30, 2009.
Written Opinion of the Int'l Searching Authority—Int'l App. No. PCT/EP2009/066082; Int'l Filing Date: Nov. 30, 2009.

*Primary Examiner* — Christopher D Koharski
*Assistant Examiner* — Philip Edwards (57) ABSTRACT The present invention generally relates to implantable medical devices, such as pacemakers, and, in particular, to a method and an implantable medical device capable of detecting the presence of noise caused by external noise sources. Voltages and/or impedances are measured over one or several electrode configurations. Based on the measured voltages and/or impedances, noise parameters are calculated, which are compared with reference values to detect the presence of noise. In another aspect of the invention, at least two different electrode configurations with different noise pick-up areas are used in the measurement. Relations between the noise parameters of the at least two vectors are calculated and compared with reference relations to detect the presence of noise.

10 Claims, 6 Drawing Sheets

METHOD AND DEVICE FOR DETECTING NOISE

TECHNICAL FIELD

The present invention generally relates to implantable medical devices, such as heart stimulators including e.g. pacemakers, and, in particular, to a method and implantable medical device capable of detecting the presence of noise caused by external noise sources.

BACKGROUND OF THE INVENTION

As is well-known, implanted medical devices, such as cardiac stimulators (pacemakers, defibrillators, etc.) commonly employ an electrode lead, extending from an implanted electronic unit, in order to sense electrical activity in the patient so as to control the electrotherapy (pacing, defibrillation, anti-tachycardia routine, etc.) administered by the implanted stimulator to the patient. The electrode lead is typically plugged at one end into the implanted electronic unit, and has an opposite end located adjacent cardiac tissue, or in the blood stream, or attached to cardiac tissue depending on the type of activity or physiological parameter being sensed. Since this electrode lead contains one or more conductors extending from the implanted device to the sensor or electrode at the tip of the lead or along the lead, the lead itself acts as an antenna and is thus susceptible to receiving signals, such as electromagnetic interference (EMI) originating from external sources. Such interference (noise) corrupts the "true" waveform originating from the sensed electrical activity and therefore when the corrupted sensed signal is analyzed within the implanted device, in order to produce a control signal for the therapy administration, the analysis may be falsified because the noise may, for example, produce spurious data points (data outliers).

For example, theft prevention systems commonly employ high-strength magnetic fields to detect the presence of a magnetic tag placed on retail merchandise. Most of these systems modulate or pulse the magnetic field in such a way that the repetition rate falls within the pass-band of cardiac sensing amplifiers.

Conventionally, problems with electro-magnetic noise have been dealt with by removing such spurious data point by different filtering methods or by means of data processing using mathematical methods. For example, in U.S. Pat. No. 5,871,509, to Noren, a median filtering method is disclosed and in US 2006/0135886 by Lippert et al, noise is reduced or removed using a mathematical compensating method.

A number of different solutions for detecting the presence of noise have been presented within the art. In, for example, U.S. Pat. No. 7,231,251 EMI detection methods and devices for implantable medical devices are shown. A magnetic sensor, e.g. a coil, detects the presence of EMI and a noise reversion mode may be initiated in which inhibition of pacing and/or delivery of defibrillation shocks are prevented while the EMI is present. The method and device disclosed in U.S. Pat. No. 7,231,251 aims at detection of noise that may affect and disturb the sensing of intrinsic cardiac activity, which often is of a low frequency below or about 100 Hz.

However, it has been found that also impedance measurements may be distorted by EMI, particularly in a frequency spectrum of about 7-10 kHz. Cardiac impedance, for example, intracardiac impedance or transthoracic impedance, have gained a rising interest during the recent years since it has been shown that cardiac impedance provides valuable information about the mechanical functioning and mechanical work of the heart. It would hence be valuable to have a solution for detection of electro-magnetic noise that affects or disturbs measurements of cardiac impedance. Furthermore, measurements of impedance in proximity of the heart such as pulmonary impedance may also be affected or disturbed by such electro-magnetic noise. Therefore, it would also be of interest of having a solution that is capable of detecting also such pulmonary impedance disturbing noise.

SUMMARY

An object of the present invention is to provide a method and implantable medical device capable of detecting the presence of noise caused by external noise sources.

Another object of the present invention is to provide a method and implantable medical device capable of detecting electro-magnetic noise that may affect or disturb measurements of cardiac impedance (e.g. intracardiac impedance) and/or pulmonary impedance.

A further object of the present invention is to provide a method and an implantable medical device that improves the quality of the measurements of cardiac impedance and/or pulmonary impedance.

These and other objects are achieved with a method and implantable medical device as defined by the independent claims. Preferred embodiments and variation of the present invention are defined by the dependent claims.

In the context of the present application, the term "noise pick-up area" refers to a physical area or field over which a specific electrode configuration, i.e. a specific measurement vector, measures e.g. voltage. In order words each measurement vector spans a pick-up area over which, for example, noise is picked up during a measurement.

According to an aspect of the present invention, there is provided an implantable medical device capable of detecting presence of electromagnetic noise. The medical device is connectable to an electrode arrangement comprising at least two electrodes and the medical device comprises a voltage measuring device adapted to measure a voltage over the at least one measurement vector. Furthermore, the medical device comprises a control module adapted to cause the voltage measuring device to measure at least one voltage over the at least one measurement vector, a calculation unit adapted to calculate at least one noise parameter for the at least one measurement vector based on the at least one voltage. Moreover, the medical device comprises a noise detecting unit adapted to:

compare the at least one noise parameter with a predetermined reference parameter value; and based on said comparison, detect whether noise that may disturb a subsequent impedance measurement is present. For example, in one embodiment, if the noise parameter exceeds the predetermined reference parameter value, it is detected that electromagnetic noise that may disturb a subsequent impedance measurement is present.

The implantable medical device may further include a current generator adapted to generate a current pulse or a series of current pulses between at least two electrodes of at least one measurement vector and an impedance calculating unit being adapted to calculate at least one impedance value based on a measured voltage resulting from the generated current pulse or a series of pulses and an amplitude value of the generated current pulse or series of pulses.

According to one embodiment, the voltage measurement device and the current generator are included in the impedance calculating unit.

According to a second aspect of the present invention, there is provided a method for detecting presence of noise using an implantable medical device being connectable to an electrode arrangement comprising at least two electrodes. The method comprises measuring a voltage over the at least one measurement vector, calculating at least one noise parameter for the at least one measurement vector based on the at least one voltage. Further, the methods comprises comparing the at least one noise parameter with a predetermined reference parameter value and, based on said comparison, it is detected whether noise that may disturb a subsequent impedance measurement is present. For example, in one embodiment, if the noise parameter exceeds the predetermined reference parameter value, it is detected that electromagnetic noise that may disturb a subsequent impedance measurement is present.

Hence, the present invention is based on the insight that the electromagnetic noise being present within the heart or in proximity to the heart of a patient caused by an external electromagnetic source can be used itself in a noise detection process. The noise affects voltage and impedance measurements very differently depending on the specific physical field pick-up area or region of the measurement vector (i.e. the noise pick-up area between the electrodes) used for the measurement. More specifically, a large physical field pick-up area will give a larger variation in the measured voltages in comparison with a small physical field pick-up area when being exposed to electromagnetical fields. This insight has also led the inventors to the idea of utilizing the mere fact that noise will be present in all field pick-up areas, independent of the size of the area, to detect such noise by comparing a measured voltage over a measurement vector with a predetermined threshold value.

According to an embodiment of the present invention, a noise detection procedure is initiated by measuring at least one voltage over each of at least two measurement vectors. The vectors are selected such that they have different noise pick-up areas and thus will be affected in different magnitude by the noise. At least one noise parameter is calculated for each measurement vector based on the measured at least one voltage for respective measurement vector and at least one relation between a respective noise parameter of two measurement vectors is calculated.

In one preferred embodiment, the relation is a quota between at least two respective vectors is calculated. Other examples of relations include a subtraction and a descending number series or other correlating factor.

Preferably, the relation is calculated at a certain frequency or frequency band, for example, 500 Hz-500 kHz.

Furthermore, it is also preferable to exclude human body induced signal frequencies through filtering, for example, signals caused by respiration activity and cardiac activity in the frequency band 0.1-3 Hz.

The at least one calculated relation is compared with one or more corresponding predetermined reference relations and, if the at least one relation exceeds one of the corresponding reference relations, it is detected that noise that may disturb a subsequent impedance measurement is present. The predetermined reference relation may be patient specific and determined based on prior measurements performed on the patient under noise free conditions or under conditions where the noise is low enough not to influence or disturb voltage or impedance measurements performed in the patient. By comparing different vectors having different noise-pick areas, it is possible to obtain an accurate and reliable detection of noise and of the presence of an external noise source. If such noise is detected, subsequent impedance measurements may be postponed until the disturbing noise has disappeared or is low enough not to disturb the measurements. Thereby, it is possible to avoid erroneous measurements.

Furthermore, by scrutinizing the difference between the calculated relation and the predetermined reference relation, it is possible to determine whether the disturbance is caused by an external noise source or by an internal noise source (e.g. heart/lung movements or biochemical voltages).

In another embodiment of the present invention, a noise detection procedure is initiated by generating a current pulse or a series of current pulses between two electrodes (one measurement vector) and at least one resulting voltage is measured over a measurement vector, which may be the same vector over which the current was generated.

Further, at least one impedance value representing a quota between a measured voltage resulting from a generated current pulse or a series of pulses and an amplitude value of the generated current pulse or series of pulses is calculated. Preferably, a series of current pulses are generated and a corresponding number of voltage samples are measured. At least one noise parameter is calculated for the measurement vector based on the at least one impedance value and the at least one noise parameter is compared with a predetermined reference parameter value. If the noise parameter exceeds the predetermined reference parameter value, detecting that noise that may disturb a subsequent or ongoing impedance measurement is present.

The predetermined reference value may be patient specific and determined based on prior measurements performed on the patient under noise free conditions or under conditions where the noise is low enough not to influence or disturb voltage or impedance measurements performed in the patient. In this embodiment, an impedance measuring session is utilized to detect whether there is disturbing noise being present. If no noise is detected, the impedance values utilized in the noise detection may be used as measurement values. On the other hand, if noise is detected, the measurements may be inhibited or stopped.

Alternatively, a noise detection impedance measurement session may be initiated and if no noise is detected the actual measurement session may be initiated. If noise is detected, the measurement session can be postponed.

According to an embodiment of the present invention, a noise detection procedure is initiated by generating a current pulse or a series of current pulses between two electrodes of at least one measurement vectors. At least one voltage is measured over each of at least two measurement vectors, wherein the at least two measurement vectors have different noise pick-up regions. At least one impedance value is calculated for each of the measurement vector and at least one noise parameter is calculated for each measurement vector based on the measured at least one impedance value for respective measurement vector.

Further, at least one relation between a respective noise parameter of two measurement vectors is calculated and is compared with a corresponding predetermined reference relation. The predetermined reference relation may be patient specific and determined based on prior measurements performed on the patient under noise free conditions or under conditions where the noise is low enough not to influence or disturb voltage or impedance measurements performed in the patient. If the calculated relation(-s) exceeds the reference relation(-s), it is detected that noise that may disturb a subsequent or ongoing impedance measurement is present. By comparing different vectors having different noise-pick areas, it is possible to obtain an accurate and reliable detection of noise and of the presence of an external noise source. If such noise is detected, subsequent impedance measurements may be postponed until the disturbing noise has disappeared or is low enough not to disturb the measurements. Thereby, it is possible to avoid erroneous measurements.

Furthermore, by scrutinizing the difference between the calculated relation and the predetermined reference relation, it is possible to determine whether the disturbance is caused by an external noise source or by an internal noise source (e.g. heart/lung movements or biochemical voltages).

According to embodiment of the present invention, the noise parameter is any one from the group including: a peak-to-peak value, a maximum amplitude, a standard deviation, a root mean square value, a spurious frequency value, or an average value.

According to embodiments of the present invention, a subsequent or ongoing impedance measurement is postponed at detection of noise.

In an embodiment of the present invention, the implantable medical device further comprises a telemetry unit adapted for two-way communication with an external device. The noise detecting unit is adapted to issue an alert signal if noise is detected and the control module is adapted to instruct the telemetry unit is transmit the alert signal to the external device.

As the skilled person realizes, steps of the methods according to the present invention, as well as preferred embodiments thereof, are suitable to realize as computer program or as a computer readable medium.

Further objects and advantages of the present invention will be discussed below by means of exemplifying embodiments.

BRIEF DESCRIPTION OF THE DRAWINGS

Exemplifying embodiments of the invention will be described below with reference to the accompanying drawings, in which.

DESCRIPTION OF EXEMPLIFYING EMBODIMENTS

The following is a description of exemplifying embodiments in accordance with the present invention. This description is not to be taken in limiting sense, but is made merely for the purposes of describing the general principles of the invention. It is to be understood that other embodiments may be utilized and structural and logical changes may be made without departing from the scope of the present invention. Thus, even though particular types of implantable medical devices such as heart stimulators will be described, e.g. biventricular pacemakers, the invention is also applicable to other types of cardiac stimulators such as dual chamber stimulators, implantable cardioverter defibrillators (ICDs), etc.

Figure 1:
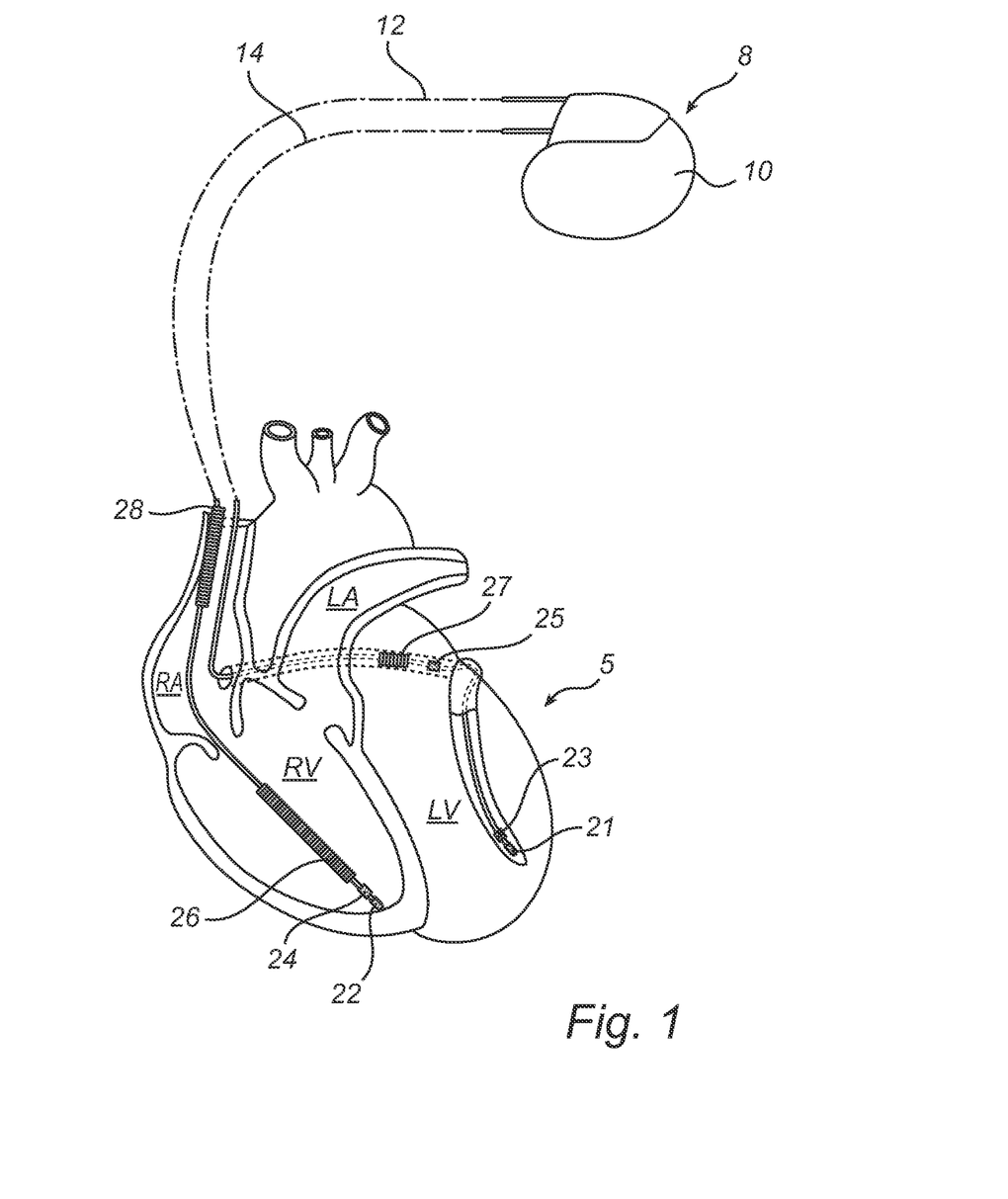
FIG. 1 is a simplified, partly cutaway view, illustrating an implantable medical device according to the present invention with a set of leads implanted into the heart of a patient.

Turning now to FIG. 1, which is a simplified schematic view of one embodiment of an implantable medical device ("IMD") 8 according to the present invention. IMD 8 has a hermetically sealed and biologically inert case 10. In this embodiment, IMD 8 is a pacemaker which is connectable to pacing and sensing leads 12, 14, in this illustrated case two leads. However, as the skilled person understands, the pacemaker may also be connected to one or several, e.g. three or more, pacing and sensing leads. IMD 8 is in electrical communication with a patient's heart 5 by way of a right ventricular lead 12 having a right ventricular (RV) tip electrode 22, a RV ring electrode 24, RV coil electrode 26, and a superior vena cava (SVC) coil electrode 28. Typically, the RV lead is transvenously inserted into the heart 5 so as to place the RV coil electrode 26 in the right ventricular apex and the SVC coil electrode 28 in the superior vena cava. Accordingly, the right ventricular lead 12 is capable of receiving cardiac signals, and delivering stimulation in the form of pacing to the right ventricle RV.

In order to sense left atrial and ventricular cardiac signals and to provide left chamber pacing therapy, IMD 8 is coupled to a "coronary sinus" lead 14 designed for placement in the coronary sinus region via the coronary sinus for positioning a distal electrode adjacent to the left atrium. As used herein, the wording "coronary sinus region" refers to the vasculature of the left ventricle, including any portion of the coronary sinus, great cardiac vein, left marginal vein, middle cardiac vein, and/or small cardiac vein or any other cardiac vein accessible via the coronary sinus. Accordingly, the coronary sinus lead 14 is designed to receive atrial and ventricular pacing signals and to deliver left ventricular pacing therapy using at least a left ventricular (LV) tip electrode 21, a LV ring electrode 23 left atrial pacing therapy using at least a LA electrode 25 and a LA electrode 27.

Furthermore, a right atrium (RA) lead 16 implanted in the atrial appendage having a RA tip electrode 19 and a RA ring electrode 17 is arranged to provide electrical communication between the right atrium (RA) and the IMD 8.

With this configuration bi-ventricular therapy can be performed. Although three medical leads are shown in FIG. 1, however, it should also be understood that additional stimulation leads (with one or more pacing, sensing, and/or shocking electrodes) may be used.

IMD 8 is an exemplary device that may use the techniques according to the invention. The invention is not limited to the device shown in FIG. 1. For example, while the pacemaker 8 is depicted as a three-chamber pacemaker, the invention can also be practiced in a single-chamber, dual-chamber, or four-chamber pacemaker. According to various embodiments of the present invention, IMD 8 detects electrical cardiac signals, including e.g. the T-wave and the R-wave.

In the embodiment of the present invention illustrated in FIG. 1, a large number of electrode configurations can be used to measure voltage and impedance. The voltage may be detected between, for example, between RV coil electrode 26 and LV ring electrode 23, or LV ring electrode 25 and the can 10. In case of impedance measurements the electrical current i(t) may be applied between the RV tip electrode 22 and the LV tip electrode 21. The voltage response may be detected between, for example, between RV coil electrode 26 and LV ring electrode 23, RA tip electrode 19 and RV ring electrode 24, and LV ring electrode 25 and the can 10. However, this is only an arbitrary example, there are, as the skilled person realizes, a large number of conceivable electrode configurations.

Figure 2:
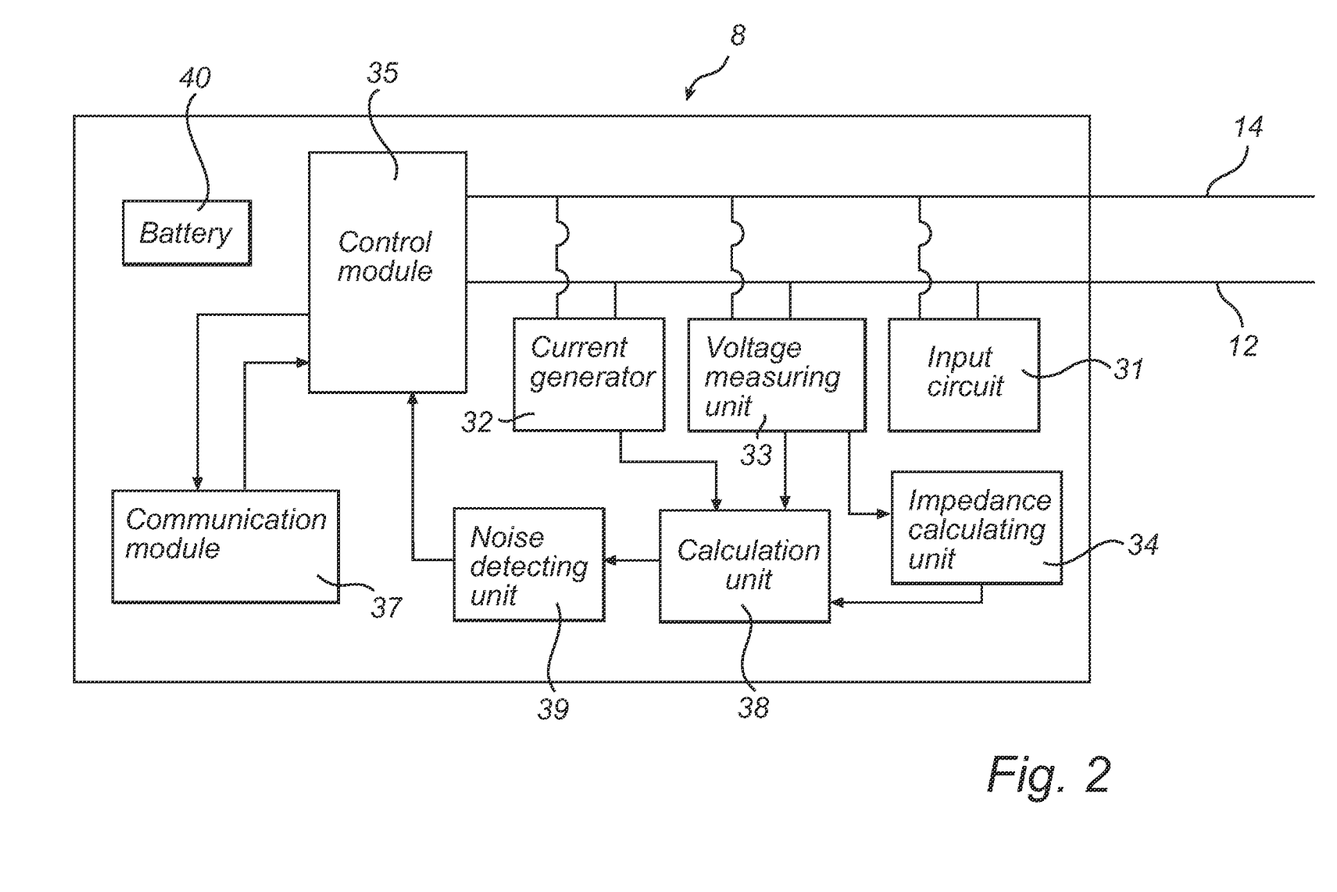
FIG. 2 is a functional block diagram form of the implantable medical device shown in FIG. 1, illustrating basic circuit elements that provide, for example, pacing stimulation in the heart and for acquiring simultaneous impedance signals from several electrode configurations according to the present invention.

FIG. 2 is a block diagram illustrating the constituent components of an IMD 8 in accordance with the general principles of the present invention. In the following, a number of different embodiments of the present invention will be discussed and similar or like part, components, modules, or circuits through the different embodiments will only be described with reference to FIG. 2. Hence, in the description of the embodiments, the description of the similar or like part, components, modules, or circuits through the different embodiments will be omitted.

According to this embodiment, the IMD 8 is a pacemaker having a microprocessor based architecture. The leads 12 and 14 are connectable to the IMD 8 and comprises, as have been illustrated in FIG. 1, one or more electrodes, such a coils, tip electrodes or ring electrodes. These electrodes are arranged to, inter alia, transmit pacing pulses for causing depolarization of cardiac tissue adjacent to the electrode(-s) generated by a pace pulse generator 32 under influence of a control module or microcontroller 35. The rate of the heart 5 is controlled by software-implemented algorithms stored within a microcomputer circuit of the control module 35. The microcomputer circuit may include a microprocessor, a system clock circuit and memory circuits including random access memory (RAM) and read-only memory (ROM). The microcomputer circuit may further include logic and timing circuitry, state machine circuitry, and I/O circuitry. Typically, the control module 35 includes the ability to process or monitor input signals (data) from an input circuit 31 as controlled by a program code stored in a designated block of memory. The details and design of the control module 35 are not critical to the present invention. Rather, any suitable control module or microcontroller 35 may be used that carries out the functions described herein. The use of micro-processor-based control circuits for performing timing and data analysis functions are well known in the art.

Detected signals from the patient's heart 5, e.g. signals indicative of natural and stimulated contractions of the heart 5, are processed in an input circuit 31 and are forwarded to the microprocessor of the control module 35 for use in logic timing determination in known manner. The input circuit 31 may include, for example, an EGM amplifier for amplifying obtained cardiac electro-gram signals.

IMD 8 comprises a communication unit 37 including an antenna (not shown), for example, a telemetry unit for uplink/downlink telemetry or RF transceiver adapted for bi-directional communication with external devices in, for example, the MICS band or ISM band.

Electrical components shown in FIG. 2 are powered by an appropriate implantable battery power source 40 in accordance with common practice in the art. For the sake of clarity, the coupling of battery power to the various components of the IMD 8 is not shown in the figures.

Furthermore, the IMD 8 comprises a current generating device 32 adapted to generate a current and apply the current between two electrodes of the medical leads 12, 14. The IMD 8 further includes a voltage measuring device 33 connected to the medical leads 12, 14 and is adapted to measure of a voltage over different electrode configurations or measurement vectors. With reference to FIG. 1, the voltage can be measured between, for example, between RV coil electrode 26 and LV ring electrode 23, or LV tip electrode 25 and the can 10. However, this is only an arbitrary example, a there are, as the skilled person realizes, a large number of conceivable electrode configurations. Depending on the specific electrode configuration chosen for a measurement, the pick-up area will be different. In the above examples, the pick-up area of the measurement vector including RV coil electrode 26 and LV ring electrode 23 will be significantly smaller than the pick-up area of the measurement vector including LV tip electrode 25 and the can 10.

An impedance calculating unit 34 is connected to the current generator 32 and to the voltage measuring device 33. The impedance calculating unit 34 is adapted to calculate impedance values based on current pulses applied over a specific electrode configuration and on resulting voltages measured over the same electrode configuration or another electrode configuration.

Figure 3:
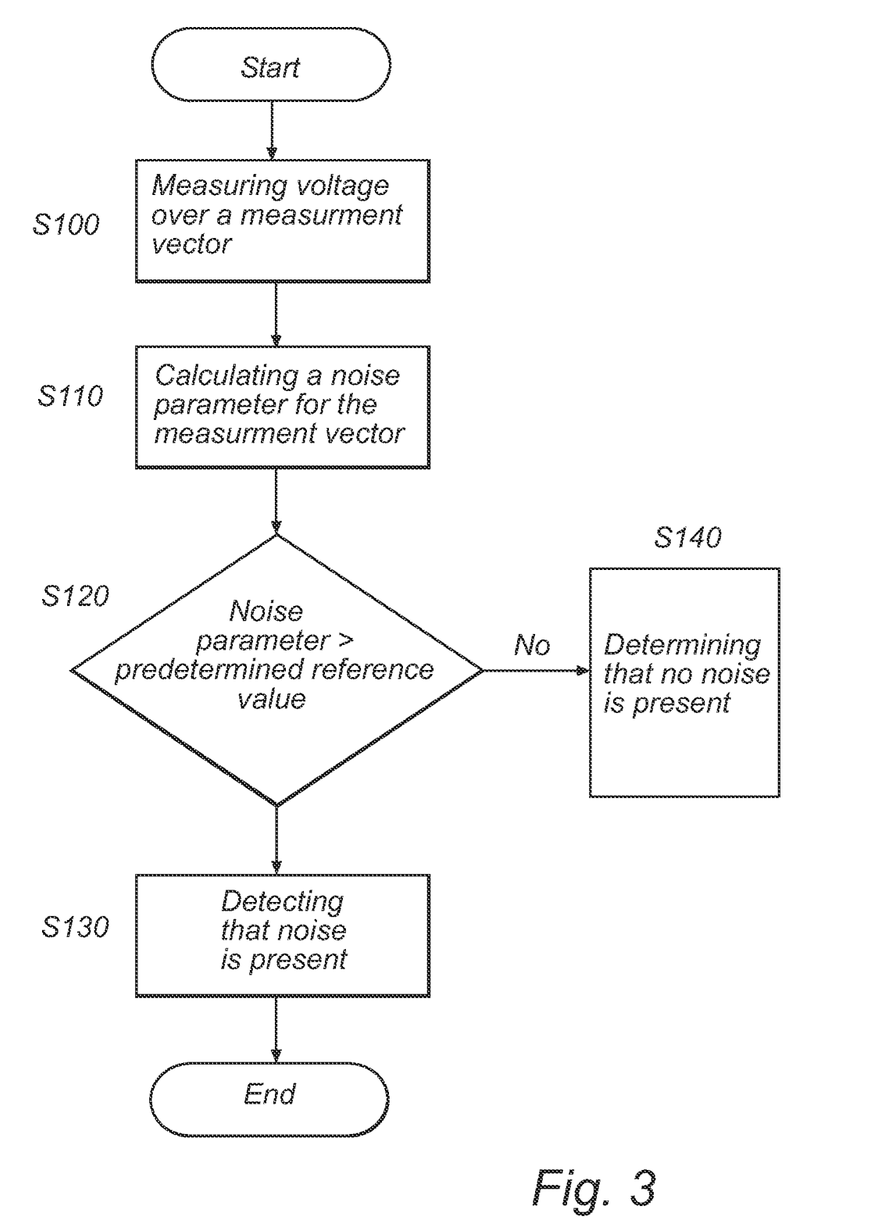
FIG. 3 schematically illustrates the principles of an embodiment of the method according to the present invention.

With reference now to the flow chart of FIG. 3, an embodiment of the method according to the present invention will be discussed. A noise detection session may be initiated as a pre-measurement step to check whether any disturbing noise is present, which may corrupt or disturb the subsequent measurements. Alternatively, a noise detection session may be initiated at regular intervals or at receipt of a noise session initiating signal at the control module 35. The noise session initiating signal may be sent manually from an external device such as a programmer wirelessly to the communication module 37. When the noise detection session is started or initiated, the control module 35 causes, at step S100, the voltage measuring device 33 to initiate a voltage measuring session. In one embodiment, the voltage is measured over a predetermined measurement vector, for example, between the RV tip electrode 22 and the LV tip electrode 21. One or several voltage samples may be acquired. Thereafter, at step S110, one noise parameter is calculated in the calculation unit 38 using the measured voltage samples. The noise parameter may be, for example, a peak-to-peak value of the voltage samples, a maximum amplitude value of the voltage samples, a standard deviation of the voltage samples, a root mean square value of the voltage samples, or a spurious frequency value, or an average value of the voltage samples. Then, at step S120, the calculated noise parameter is compared with a predetermined reference parameter value in the noise detecting unit 39. The predetermined reference parameter value may be patient specific and determined based on prior measurements performed on the patient under noise free conditions or under conditions where the noise is low enough not to influence or disturb voltage or impedance measurements performed in the patient. If the calculated noise parameter exceeds the predetermined reference parameter value, the noise detection unit 39 detects, at step S130, that noise is present that may disturb or corrupt a subsequent impedance measurement.

According to an embodiment, if such potentially disturbing noise is detected, the control module 35 is adapted to instruct the impedance measuring unit 34 to postpone subsequent impedance measurements.

In a further embodiment, the noise detecting unit 39 is adapted to issue an alert signal if noise is detected and the control module 35 is adapted to instruct the communication module 37 to transmit the alert signal to an external device.

If the calculated noise parameter is below the predetermined noise threshold parameter in the comparison at step S120, the procedure continues to step S140 where the noise detection unit 39 determines that no noise is present. Thereafter, voltage or impedance measurement can be performed without the risk of being corrupted by noise.

Figure 4:
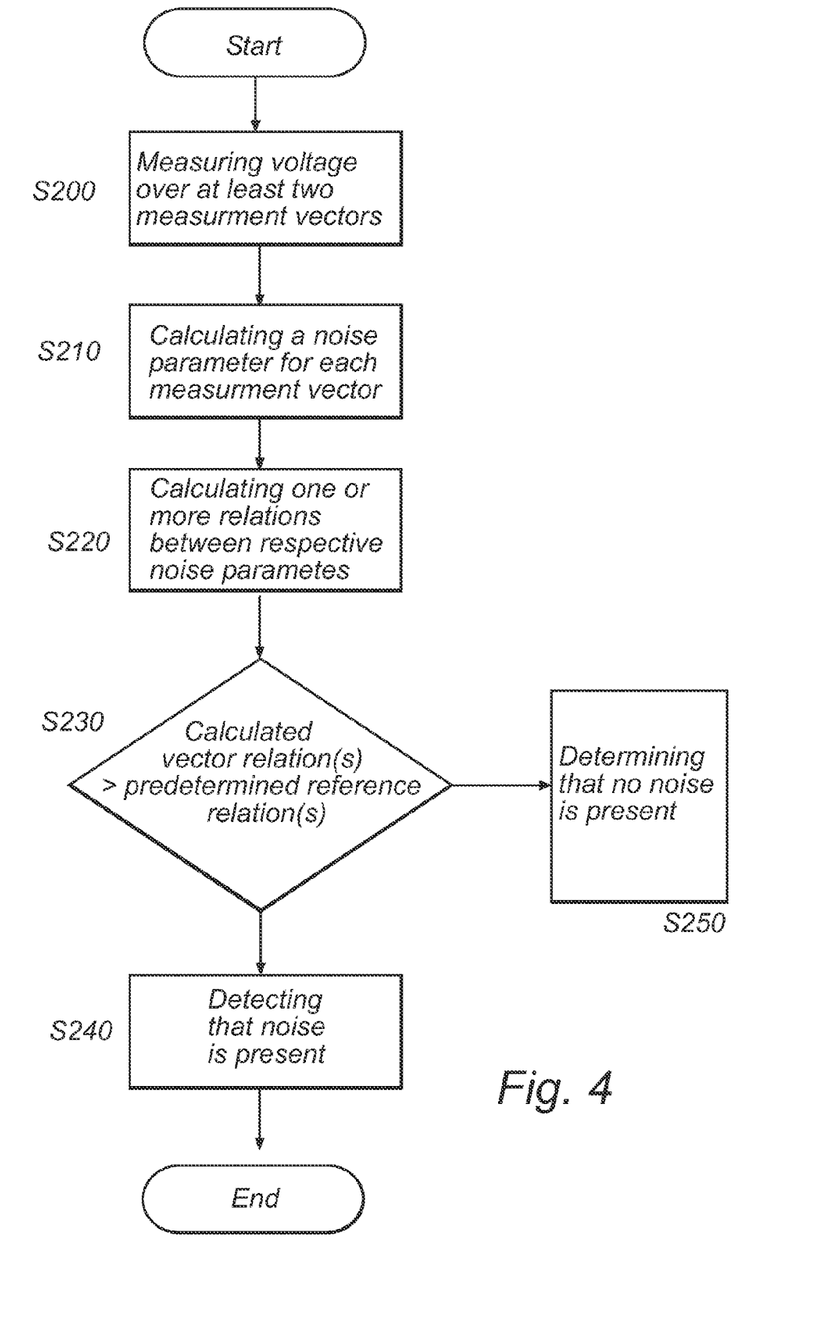
FIG. 4 schematically illustrates the principles of another embodiment of the method according to the present invention.

With reference to the flow chart of FIG. 4, an embodiment of the method according to the present invention will be discussed. A noise detection session may be initiated as a pre-measurement step to check whether any disturbing noise is present, which may corrupt or disturb the subsequent measurements. Alternatively, a noise detection session may be initiated at regular intervals or at receipt of a noise session initiating signal at the control module 35. The noise session initiating signal may be sent manually from an external device such as a programmer wirelessly to the communication module 37. When the noise detection session is started or initiated, the control module 35 causes, at step S200, the voltage measuring device 33 to initiate a voltage measuring session. In this embodiment, a voltage is measured over at least two measurement vectors, for example, between the RV tip electrode 22 and the LV tip electrode 21 and the RV coil electrode 26 and the case 10. The vectors are selected such that they have different noise pick-up regions. One or several voltage samples may be acquired for each vector.

Thereafter, at step S210, one noise parameter is calculated for each vector in the calculation unit 38 using the measured voltage samples for respective vector. The noise parameter may be, for example, a peak-to-peak value of the voltage samples, a maximum amplitude value of the voltage samples, a standard deviation of the voltage samples, a root mean square value of the voltage samples, or a spurious frequency value, or an average value of the voltage samples.

Then, at step S220, at least one relation between a respective noise parameter of the respective measurement vectors is calculated. In one preferred embodiment, the relation is a quota between two respective vectors is calculated. Other examples of relations include a subtraction between the noise parameters of the respective vectors and a descending number series or other correlating factor.

Preferably, the relation is calculated at a certain frequency or frequency band, for example, 500 Hz-500 kHz.

Furthermore, it is also preferable to exclude human body induced signal frequencies through filtering, for example, signals caused by respiration activity and cardiac activity in the frequency band 0.1-3 Hz.

Thereafter, at step S230, the calculated relation is compared with one ore more corresponding predetermined reference relations in the noise detecting unit 39. The predetermined reference relation(-s) may be patient specific and determined based on prior measurements performed on the patient under noise free conditions or under conditions where noise is low enough not to influence or disturb voltage or impedance measurements performed in the patient. If the calculated relation exceeds the predetermined reference value, the noise detection unit 39 detects, at step S240, that noise is present that may disturb or corrupt a subsequent impedance measurement.

According to an embodiment, if such potentially disturbing noise is detected, the control module 35 is adapted to instruct the impedance measuring unit 34 to postpone subsequent impedance measurements.

In a further embodiment, the noise detecting unit 39 is adapted to issue an alert signal if noise is detected and the control module 35 is adapted to instruct the communication module 37 to transmit the alert signal to an external device.

If the calculated relation(-s) is below the predetermined reference value in the comparison at step S230, the procedure continues to step S250 where the noise detection unit 39 determines that no noise is present. Thereafter, voltage or impedance measurement can be performed without the risk of being corrupted by noise.

In one preferred embodiment, voltage samples from the following vectors are measured: RV tip electrode 22 and RV ring electrode 24, RV coil electrode 26 and case 10, RV coil electrode 26 and SVC (superior vena cava) electrode (not shown), and SVC electrode and case 10. The maximum amplitude is calculated for each vector. Thereafter, the maximum amplitude for each vector is compared: the maximum amplitude for RV coil electrode 26 and case 10 is compared with the maximum amplitude for SVC (not shown) and case 10, the maximum amplitude for RV coil electrode 26 and SVC is compared with RV coil electrode 26 and case 10, RV tip electrode 22 and RV ring electrode 24 is compared with RV coil electrode 26 and SVC. The following should apply in order to detect that no noise or noise of a low strength is present:

the maximum amplitude for RV coil electrode 26 and case 10 should be the largest. For example, a relation with each of the other vectors may be calculated and compared with corresponding reference relations where the reference relations is the corresponding relations obtained at noise free conditions in the patient;

the maximum amplitude for SVC (not shown) and case 10 should be smaller than the maximum amplitude for RV coil electrode 26 and case 10. Preferably, the relation between the maximum amplitude for SVC (not shown) and case 10 and the maximum amplitude for RV coil electrode 26 and case 10 should be lower than a predetermined reference relation where the reference relation is the corresponding relation obtained at noise free conditions in the patient;

the maximum amplitude for RV coil electrode 26 and SVC should be smaller than the maximum amplitude for RV coil electrode 26 and case 10. Preferably, the relation between the maximum amplitude for RV coil electrode 26 and SVC and the maximum amplitude for RV coil electrode 26 and case 10 should be lower than a predetermined reference relation where the reference relation is the corresponding relation obtained at noise free conditions in the patient; and the maximum amplitude for RV tip electrode 22 and RV ring electrode 24 should be significantly smaller than the maximum amplitude for RV coil electrode 26 and SVC. Preferably, the relation between the maximum amplitude for RV tip electrode 22 and RV ring electrode 24 than the maximum amplitude for RV coil electrode 26 and SVC should be lower than a predetermined reference relation where the reference relation is the corresponding relation obtained at noise free conditions in the patient.

Hence, in this specific embodiment of the present invention, a number of relations are compared with reference relations in order to determine whether noise is present.

Figure 5:
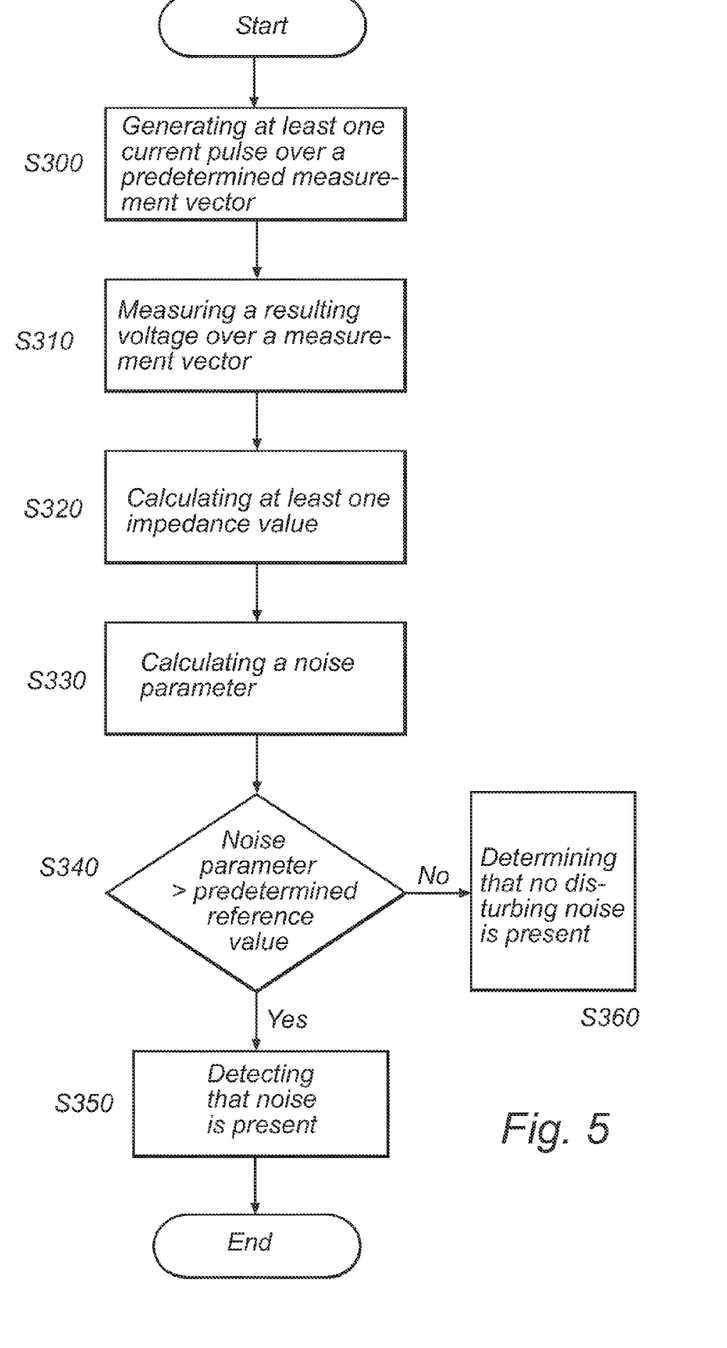
FIG. 5 schematically illustrates the principles of a further embodiment of the method according to the present invention.

Referring now to FIG. 5, another embodiment of the method according to the present invention will be discussed. A noise detection session may be initiated as a pre-measurement step to check whether any disturbing noise is present, which may corrupt or disturb the subsequent measurements. Alternatively, a noise detection session may be initiated at regular intervals or at receipt of a noise session initiating signal at the control module 35. The noise session initiating signal may be sent manually from an external device such as a programmer wirelessly to the communication module 37. When the noise detection session is started or initiated, the control module 35 instructs, at step S300, the current generator 32 to generate a current pulse or a series of current pulses between at least two electrodes of one measurement vector, and instructs, at step S310, the voltage measuring device 33 to measure at least one resulting voltage over a measurement vector, which may be the same vector the current was generated over or another vector. One or several voltage samples may be measure by the voltage measuring device 33. For example, the current may be injected between the RV tip electrode 22 and the LV tip electrode 21 and the voltage may be measured over the same vector.

Then, at step S320, the impedance calculating unit 34 calculates at least one impedance value representing a quota between a measured voltage resulting from a generated current pulse or a series of voltages resulting from a series of generated pulses and an amplitude value of the generated current pulse or series of current pulses.

Thereafter, at step S330, one noise parameter is calculated for the vector in the calculation unit 38 using the calculated impedance value (-s). The noise parameter may be, for example, a peak-to-peak value of a respective absolute value of the impedance values, a maximum amplitude value of a respective absolute value of the impedance values, a standard deviation of a respective absolute value of the impedance values, a root mean square value of a respective absolute value of the impedance values, or a spurious frequency value, or an average value of a respective absolute value of the impedance values.

At step S340, the calculated noise parameter is compared with a corresponding predetermined reference value in the noise detecting unit 39. The predetermined reference value may be patient specific and determined based on prior measurements performed on the patient under noise free conditions or under conditions where noise is low enough not to influence or disturb voltage or impedance measurements performed in the patient. If the calculated noise parameter exceeds the predetermined reference value, the noise detection unit 39 detects, at step S350, that noise is present that has influenced the present impedance value obtained during the ongoing measurements and thus may disturb or corrupt a subsequent impedance measurement.

According to an embodiment, if such disturbing noise is detected, the control module 35 is adapted to instruct the impedance measuring unit 34 to postpone subsequent impedance measurements.

In a further embodiment, the noise detecting unit 39 is adapted to issue an alert signal if noise is detected and the control module 35 is adapted to instruct the communication module 37 to transmit the alert signal to an external device.

If the calculated noise parameter is below the predetermined reference value in the comparison at step S340, the procedure continues to step S360 where the noise detection unit 39 determines that no noise is present. Thereafter, voltage or impedance measurement can be continued without the risk of being corrupted by disturbing noise.

Figure 6:
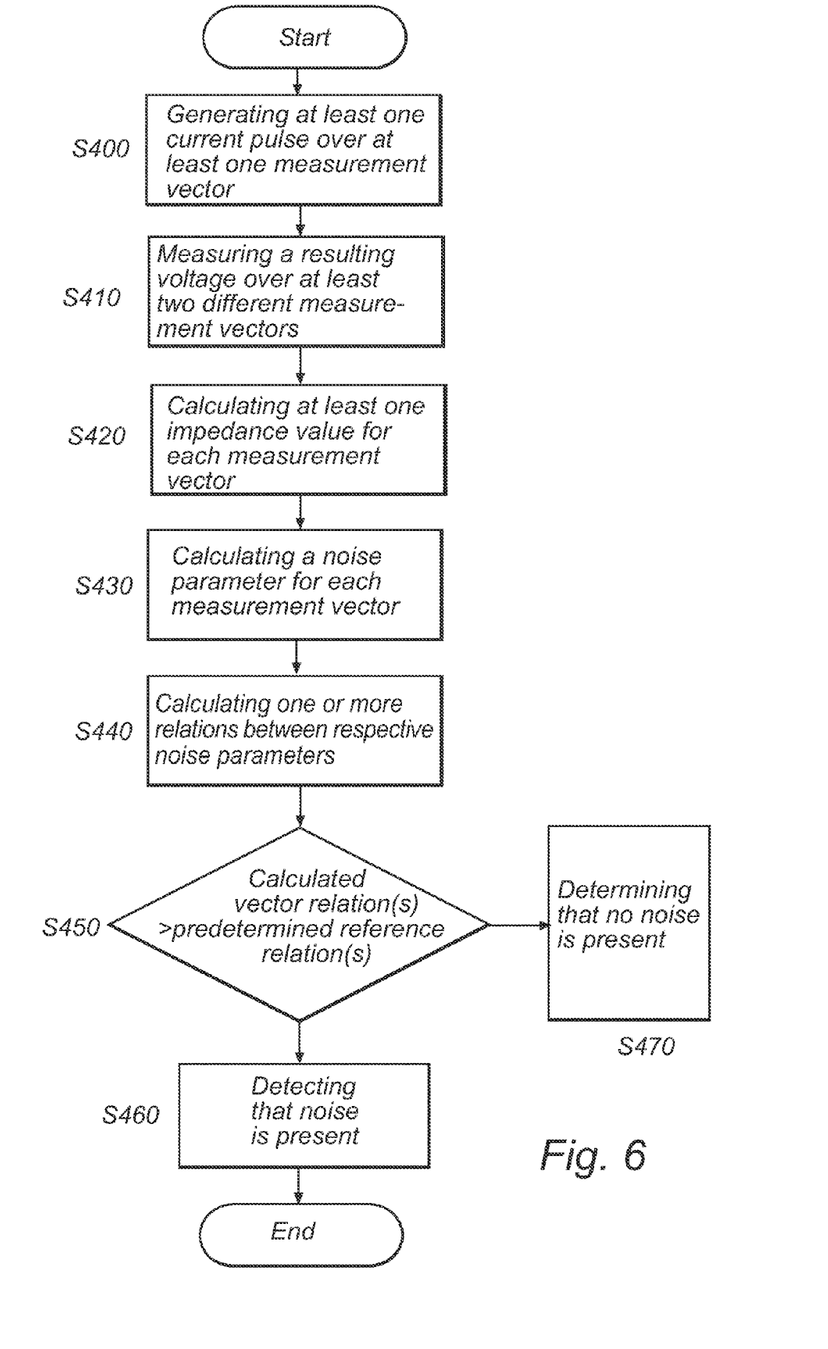
FIG. 6 schematically illustrates the principles of yet another embodiment of the method according to the present invention.

With reference to the flow chart of FIG. 6, a further embodiment of the method according to the present invention will be discussed. A noise detection session may be initiated as a pre-measurement step to check whether any disturbing noise is present, which may corrupt or disturb the subsequent measurements. Alternatively, a noise detection session may be initiated at regular intervals or at receipt of a noise session initiating signal at the control module 35. The noise session initiating signal may be sent manually from an external device such as a programmer wirelessly to the communication module 37.

When the noise detection session is started or initiated, the control module 35 instructs, at step S400, the current generator 32 to generate a current pulse or a series of current pulses between two electrodes of at least one measurement vector, but preferably two respective electrodes of at least two different vectors. For example, between the RV tip electrode 22 and the LV tip electrode 21 and the RV coil electrode 26 and the case 10. Thereafter, the control module 35 instructs, at step S410, the voltage measuring device 33 to measure resulting voltages over at least two different measurement vectors. In this embodiment, a resulting voltage is measured over at least two measurement vectors, for example, between the RV tip electrode 22 and the LV tip electrode 21 and the RV coil electrode 26 and the case 10. The vectors are selected such that they have different noise pick-up regions. One or several voltage samples may be acquired for each vector.

Subsequently, at step S420, at least one impedance value for each respective measurement vector is calculated by the impedance calculating unit 34 using the generated current pulse or series of pulses and the measured resulting voltages for respective vector. Preferably, a series of current pulses are generated and a corresponding number of voltage samples are measured.

Thereafter, at step S430, one noise parameter is calculated for each vector in the calculation unit 38 using the calculated impedance values for respective vector. The noise parameter may be, for example, a peak-to-peak value of a respective absolute value of the impedance values, a maximum amplitude value of a respective absolute value of the impedance values, a standard deviation of a respective absolute value of the impedance values, a root mean square value of a respective absolute value of the impedance values, or a spurious frequency value, or an average value of a respective absolute value of the impedance values.

Then, at step S440, at least one relation between a respective noise parameter of the respective measurement vectors is calculated. In one embodiment of the present invention, the relation is a quota between the respective noise parameters. Other examples of relations include a subtraction between the noise parameters of the respective vectors and a descending number series or other correlating factor.

Preferably, the relation is calculated at a certain frequency or frequency band, for example, 500 Hz-500 kHz. Furthermore, it is also preferable to exclude human body induced signal frequencies through filtering, for example, signals caused by respiration activity and cardiac activity in the frequency band 0.1-3 Hz.

Thereafter, at step S450, the calculated at least one relation is compared with a corresponding predetermined reference relation in the noise detecting unit 39. The predetermined reference relation may be patient specific and determined based on prior measurements performed on the patient under noise free conditions or under conditions where noise is low enough not to influence or disturb voltage or impedance measurements performed in the patient. If the calculated relation exceeds the predetermined reference relation, the noise detection unit 39 detects, at step S460, that noise is present that has disturbed the ongoing impedance measurement and thus may disturb or corrupt a subsequent impedance measurement.

According to an embodiment, if such potentially disturbing noise is detected, the control module 35 is adapted to instruct the impedance measuring unit 34 to postpone subsequent impedance measurements.

In a further embodiment, the noise detecting unit 39 is adapted to issue an alert signal if noise is detected and the control module 35 is adapted to instruct the communication module 37 to transmit the alert signal to an external device.

If the calculated relation is below the predetermined reference relation in the comparison at step S450, the procedure continues to step S470 where the noise detection unit 39 determines that no noise is present. Thereafter, voltage or impedance measurement can be performed without the risk of being corrupted by noise.

In one preferred embodiment, impedance values from the following vectors are calculated: RV tip electrode 22 and RV ring electrode 24, RV coil electrode 26 and case 10, RV coil electrode 26 and SVC (superior vena cava) electrode (not shown), and SVC electrode and case 10. The maximum amplitude of the absolute value of the impedance is calculated for each vector. Thereafter, the maximum amplitude for each vector is compared: the maximum amplitude for RV coil electrode 26 and case 10 is compared with the maximum amplitude for SVC (not shown) and case 10, the maximum amplitude for RV coil electrode 26 and SVC is compared with RV coil electrode 26 and case 10, RV tip electrode 22 and RV ring electrode 24 is compared with RV coil electrode 26 and SVC. The following should apply in order to detect that no noise or noise of a low strength is present:

the maximum amplitude for RV coil electrode 26 and case 10 should be the largest. For example, a relation with each of the other vectors may be calculated and compared with corresponding reference relations where the reference relations is the corresponding relations obtained at noise free conditions in the patient;

the maximum amplitude for SVC (not shown) and case 10 should be smaller than the maximum amplitude for RV coil electrode 26 and case 10. Preferably, the relation between the maximum amplitude for SVC (not shown) and case 10 and the maximum amplitude for RV coil electrode 26 and case 10 should be lower than a predetermined reference relation where the reference relation is the corresponding relation obtained at noise free conditions in the patient;

the maximum amplitude for RV coil electrode 26 and SVC should be smaller than the maximum amplitude for RV coil electrode 26 and case 10. Preferably, the relation between the maximum amplitude for RV coil electrode 26 and SVC and the maximum amplitude for RV coil electrode 26 and case 10 should be lower than a predetermined reference relation where the reference relation is the corresponding relation obtained at noise free conditions in the patient; and the maximum amplitude for RV tip electrode 22 and RV ring electrode 24 should be significantly smaller than the maximum amplitude for RV coil electrode 26 and SVC. Preferably, the relation between the maximum amplitude for RV tip electrode 22 and RV ring electrode 24 than the maximum amplitude for RV coil electrode 26 and SVC should be lower than a predetermined reference relation where the reference relation is the corresponding relation obtained at noise free conditions in the patient.

Hence, in this specific embodiment of the present invention, a number of relations are compared with reference relations in order to determine whether noise is present.

Although modifications and changes may be suggested by those skilled din the art, it is intended that all changes and modifications as reasonably and properly come within the scope of the contribution to the art made by this invention is embodied in the description and in the claims.

The invention claimed is:

1. An implantable medical device capable of detecting presence of noise, said device being connectable to an electrode arrangement comprising a plurality of electrodes adapted to define one or more measurement vectors, each having a noise pick-up region, said device comprising:
 a voltage measuring device adapted to measure a voltage;
 a control module adapted to cause the voltage measuring device to measure at least one voltage over each of at least two measurement vectors, wherein the at least two measurement vectors have different noise pick-up regions;
 a calculation unit adapted to:
  calculate at least one noise parameter for each measurement vector based on the measured at least one voltage for respective measurement vector; and
  calculate at least one relation between a respective noise parameter of two measurement vectors; and
 a noise detecting unit adapted to:
  compare the at least one relation with at least one corresponding predetermined reference relation; and
  if the at least one relation exceeds the at least one corresponding reference relation, detect that noise that may disturb a subsequent impedance measurement is present.

2. The implantable medical device of claim 1, further comprising:
 a current generator adapted to generate a current pulse or a series of current pulses between at least two electrodes of each of the at least two measurement vectors; and
 an impedance calculating unit being adapted to calculate at least one impedance value representing a quota between a measured voltage resulting from a generated current pulse or a series of pulses and the generated current pulse or series of current pulses;
 wherein:
 the voltage measuring device is adapted to measure at least one resulting voltage over each of the at least two measurement vectors; and
 the control module is adapted to cause the impedance measuring unit to determine at least one impedance value for each of the at least two measurement vectors;
 the calculation unit is adapted to:
  calculate at least one noise parameter for each of the at least two measurement vectors based on the measured at least one impedance value for the respective measurement vector; and
  calculate at least one relation between a respective noise parameter of two measurement vectors; and
 the noise detecting unit is adapted to:
  compare the at least one relation with at least one corresponding predetermined reference relation; and
  if the relation exceeds the at least one corresponding reference relation, detect that noise that may disturb a subsequent or ongoing impedance measurement is present.

3. The implantable medical device of claim 1, wherein the noise parameter is any one from the group including: a peak-to-peak value, a maximum amplitude, a standard deviation, a root mean square value, a spurious frequency value, or an average value.

4. The implantable medical device of claim 1, wherein the calculation unit is adapted to calculate the relation between respective noise parameters as: a quota, a subtraction, or a descending number series.

5. The implantable medical device of claim 1, wherein the control module is adapted to instruct the impedance measuring unit to postpone ongoing or subsequent impedance measurements at detection of noise.

6. The implantable medical device of claim 1, further comprising a telemetry unit adapted for two-way communication with an external device, wherein the noise detecting unit is adapted to issue an alert signal if noise is detected, and wherein the control module is adapted to instruct the telemetry unit is transmit the alert signal to the external device.

7. The method of claim 1 wherein the first noise parameter and the second noise parameter comprise a peak-to-peak value, a maximum amplitude, a standard deviation, a root mean square value, a spurious frequency value, or an average value.

8. The method of claim 1 wherein the calculated relation comprises a quota, a difference, or a descending number series.

9. The method of claim 1 wherein:
the first measurement vector has a larger noise pick-up region than the second measurement vector;
calculating a relation comprises determining which of the first noise parameter and the second noise parameter is greater; and
the predetermined reference relation comprises the first noise parameter being greater than the second noise parameter.

10. An implantable medical device comprising:
a plurality of electrodes adapted to define one or more measurement vectors, each measurement vector having a noise pick-up region of a different size; and
a processor configured to:
   measure an electrical characteristic of each of a first measurement vector and a second measurement vector;
   calculate a first noise parameter based on the electrical characteristic of the first measurement vector;
   calculate a second noise parameter based on the electrical characteristic of the second measurement vector;
   calculate a relation between the first noise parameter and the second noise parameter;
   compare the calculated relation to a predetermined reference relation; and
   detect the presence of noise if the calculated relation does not satisfy the predetermined reference relation.

* * * * *